(12) United States Patent
Wang et al.

(10) Patent No.: US 12,152,183 B2
(45) Date of Patent: Nov. 26, 2024

(54) FLUORESCENT MATERIAL AND METHOD OF SYNTHESIZING THEREOF

(71) Applicant: Wuhan China Star Optoelectronics Semiconductor Display Technology Co., Ltd., Wuhan (CN)

(72) Inventors: Xu Wang, Wuhan (CN); Yanjie Wang, Wuhan (CN)

(73) Assignee: Wuhan China Star Optoelectronics Semiconductor Display Technology Co., Ltd., Wuhan (CN)

( * ) Notice: Subject to any disclaimer, the term of this patent is extended or adjusted under 35 U.S.C. 154(b) by 1116 days.

(21) Appl. No.: 16/957,396

(22) PCT Filed: Apr. 14, 2020

(86) PCT No.: PCT/CN2020/084673
§ 371 (c)(1),
(2) Date: Jun. 24, 2020

(87) PCT Pub. No.: WO2021/196274
PCT Pub. Date: Oct. 7, 2021

(65) Prior Publication Data
US 2023/0114209 A1 Apr. 13, 2023

(30) Foreign Application Priority Data
Mar. 31, 2020 (CN) .......................... 202010246016.6

(51) Int. Cl.
| | | |
|---|---|---|
| C09K 11/06 | (2006.01) | |
| C07D 471/22 | (2006.01) | |
| C07F 5/02 | (2006.01) | |
| H10K 50/11 | (2023.01) | |
| H10K 85/30 | (2023.01) | |
| H10K 85/60 | (2023.01) | |

(52) U.S. Cl.
CPC ............ *C09K 11/06* (2013.01); *C07D 471/22* (2013.01); *C07F 5/02* (2013.01); *H10K 85/322* (2023.02); *H10K 85/6572* (2023.02); *H10K 85/658* (2023.02); *C09K 2211/1007* (2013.01); *C09K 2211/1011* (2013.01); *C09K 2211/1018* (2013.01); *H10K 50/11* (2023.02)

(58) Field of Classification Search
None
See application file for complete search history.

(56) References Cited

U.S. PATENT DOCUMENTS

| | | |
|---|---|---|
| 2012/0232241 A1 | 9/2012 | Stoessel |
| 2013/0181202 A1 | 7/2013 | Yofu |
| 2014/0374733 A1 | 12/2014 | Hirai |
| 2015/0129861 A1 | 5/2015 | Hamano |
| 2020/0006668 A1 | 1/2020 | Sun |
| 2020/0006669 A1 | 1/2020 | Sun |
| 2020/0044159 A1 | 2/2020 | Yamatani |

(Continued)

FOREIGN PATENT DOCUMENTS

| | | |
|---|---|---|
| CN | 107266484 A | 10/2017 |
| CN | 110437229 A | 11/2019 |
| CN | 110746426 A | 2/2020 |

(Continued)

OTHER PUBLICATIONS

Yamamoto et al., "Synthesis of Three-Dimensional Butterfly Slit-Cyclobisazaanthracenes and Hydrazinobisanthenes through One-Step Cyclodimerization and Their Properties", Chemistry—A European Journal (2016), 22(2), 663-671. (Year: 2016).*
Chinese Office Action issued in corresponding Chinese Patent Application No. 202010246016.6 dated Jan. 11, 2021, pp. 1-6.
Chinese Office Action issued in corresponding Chinese Patent Application No. 202010246016.6 dated Aug. 2, 2021, pp. 1-4.
International Search Report in International application No. PCT/CN2020/084673, mailed on Nov. 16, 2020.
Written Opinion of the International Search Authority in International application No. PCT/CN2020/084673, mailed on Nov. 16, 2020.

(Continued)

*Primary Examiner* — Dylan C Kershner
(74) *Attorney, Agent, or Firm* — PV IP PC; Wei Te Chung

(57) ABSTRACT

A fluorescent material and a method of synthesizing thereof are provided. The fluorescent material includes a formula (1) as follows:

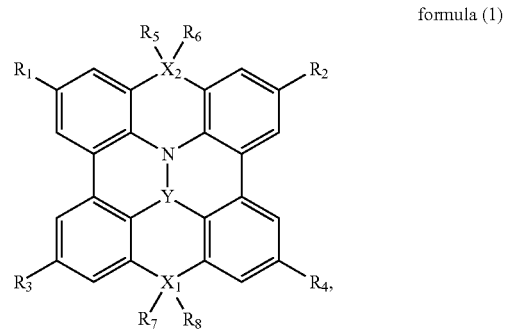

formula (1)

and Y is N or B; $X_1$ and $X_2$ are the same or different; $X_1$ and $X_2$ are selected from C or Si; $R_1$, $R_2$, $R_3$, and $R_4$ are the same or different; $R_1$, $R_2$, $R_3$, and $R_4$ are selected from a hydrogen atom, an alkyl group, an aromatic hydrocarbon group, or a heteroaryl group; $R_5$, $R_6$, $R_7$, and $R_8$ are the same or different; $R_5$, $R_6$, $R_7$, and $R_8$ are selected from an alkyl group, an aromatic hydrocarbon group, or a heteroaryl group; or $R_5$ and $R_6$ form a cyclic group; or $R_7$ and $R_8$ form a cyclic group.

9 Claims, 1 Drawing Sheet

(56) References Cited

U.S. PATENT DOCUMENTS

2023/0010535 A1* 1/2023 Diev .................. C07F 5/027

FOREIGN PATENT DOCUMENTS

KR 20140034710 A 3/2014
KR 20180008283 A 1/2018

OTHER PUBLICATIONS

European Office Action issued in corresponding European Patent Application No. 20859640.3 dated Jun. 3, 2024, pp. 1-10.
Chemistry A European Journal Nov. 30, 2015 Synthesis of Three-Dimensional Butterfly Slit-Cyclobisazaanthracenes and Hydrazinobisanthenes through One-Step Cyclodimerization and Their Properties Yamamoto, Koji, etc.

* cited by examiner

FLUORESCENT MATERIAL AND METHOD OF SYNTHESIZING THEREOF

RELATED APPLICATIONS

This application is a National Phase of PCT Patent Application No. PCT/CN2020/084673 having International filing date of Apr. 14, 2020, which claims the benefit of priority of Chinese Patent Application No. 202010246016.6 filed on Mar. 31, 2020. The contents of the above applications are all incorporated by reference as if fully set forth herein in their entirety.

FILED AND BACKGROUND OF THE INVENTION

The present invention relates to the field of organic luminescent materials, and more particularly, to a fluorescent material and a method of a synthesizing therefore.

With the continuous development of organic light-emitting diode (OLED) technology in the field of display and lighting, people pay more attention to core materials, especially organic electroluminescent materials. The early luminescent materials used in OLEDs are traditional fluorescent materials. A ratio of singlet and triplet excitons in OLEDs is 1:3, and the traditional fluorescent materials can only use singlet excitons to emit light. Therefore, a theoretical quantum efficiency of traditional fluorescent materials used in OLEDs is 25%. In theoretical research, organic fluorescent materials have made great progress, for example, Professor Adachi has developed thermally delayed fluorescent materials (TADF), which realizes the intersystem crossing of excitons from the triplet state to the singlet state, and the internal quantum efficiency can reach 100% in theoretical research. However, the actual situation is not, it depends on the ratio of the number of electrons transitioning from the singlet state to the ground state per unit time and the number of electrons that the triplet state crosses to the singlet state. If the electron in the triplet state does not quickly cross to the singlet state, it will gradually return to the ground state in the form of heat generation, resulting in energy loss. In additionally, the spectrum is too wide, so the emitted light color is impure. Therefore, the luminous efficiency of the blue light-emitting material is low, the life is short, and the application of the TADF material in the display field is limited.

The OLEDs are produced by red, green, and blue organic light-emitting molecules to produce three primary colors and then display various colors. Among them, blue light-emitting materials have short emission wavelength and wide energy band gap, so it is difficult to inject carriers, and the molecular structure and carrier mobility of the blue light-emitting materials are also relatively poor.

Coupled with the reason for the visual sensitivity function, the luminous efficiency and lifetime of blue light-emitting materials are much lower than those of red light-emitting and green light-emitting materials. Blue light-emitting performance has become an inevitable shortcoming that affects OLED displays. Currently, the fluorescent materials with triple-triple annihilation (TTA) properties increase the total amount of singlet electrons due to the annihilation effect of electrons in the triplet state, and the theoretical internal quantum efficiency can reach 62.5%, so that the fluorescent materials have also been received extensive attention in the display field. Therefore, the demand for blue light-emitting materials with excellent performance in the OLED display field provides opportunities and challenges for the development and design of fluorescent materials with the TTA properties.

SUMMARY OF THE INVENTION

In order to solve the problem in the prior art, a deep-blue fluorescent material with triple-triple annihilation (TTA) properties is provided.

A fluorescent material comprises a formula (1) as follows:

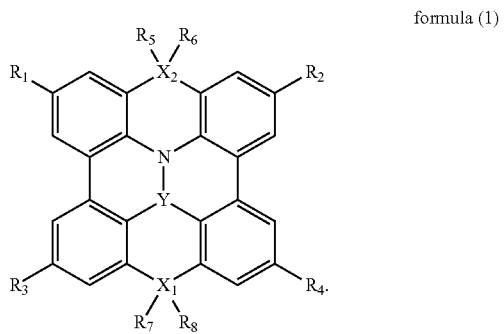

formula (1)

$Y$ is N or B; $X_1$ and $X_2$ are the same or different; $X_1$ and $X_2$ are selected from C or Si; $R_1$, $R_2$, $R_3$, and $R_4$ are the same or different; $R_1$, $R_2$, $R_3$, and $R_4$ are selected from a hydrogen atom, an alkyl group, an aromatic hydrocarbon group, or a heteroaryl group; $R_5$, $R_6$, $R_7$, and $R_8$ are the same or different; $R_5$, $R_6$, $R_7$, and $R_8$ are selected from an alkyl group, an aromatic hydrocarbon group, or a heteroaryl group; or $R_5$ and $R_6$ form a cyclic group; or $R_7$ and $R_8$ form a cyclic group.

In one embodiment, $R_1$, $R_2$, $R_3$, $R_4$, $R_5$, $R_6$, $R_7$, and $R_8$ are selected from $C_6$-$C_{50}$ an aromatic hydrocarbon group, a heteroaryl group, a $C_1$-$C_{20}$ alkyl group; or $R_5$ and $R_6$ form a $C_6$-$C_{50}$ cyclic group; or $R_7$ and $R_8$ form a $C_6$-$C_{50}$ cyclic group.

In one embodiment, $R_5$ and $R_6$ form a $C_6$-$C_{50}$ cyclic group having an aryl substituent; or $R_7$ and $R_8$ form a $C_6$-$C_{50}$ cyclic group having an aryl substituent.

In one embodiment, $R_1$, $R_2$, $R_3$, $R_4$, $R_5$, $R_6$, $R_7$, and $R_8$ are selected from one of formulas as follows:

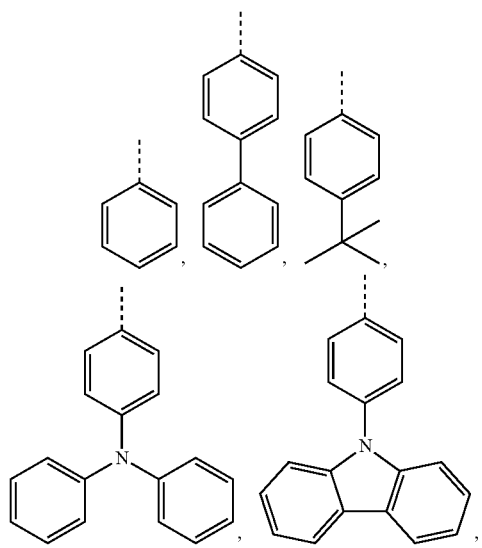

-continued

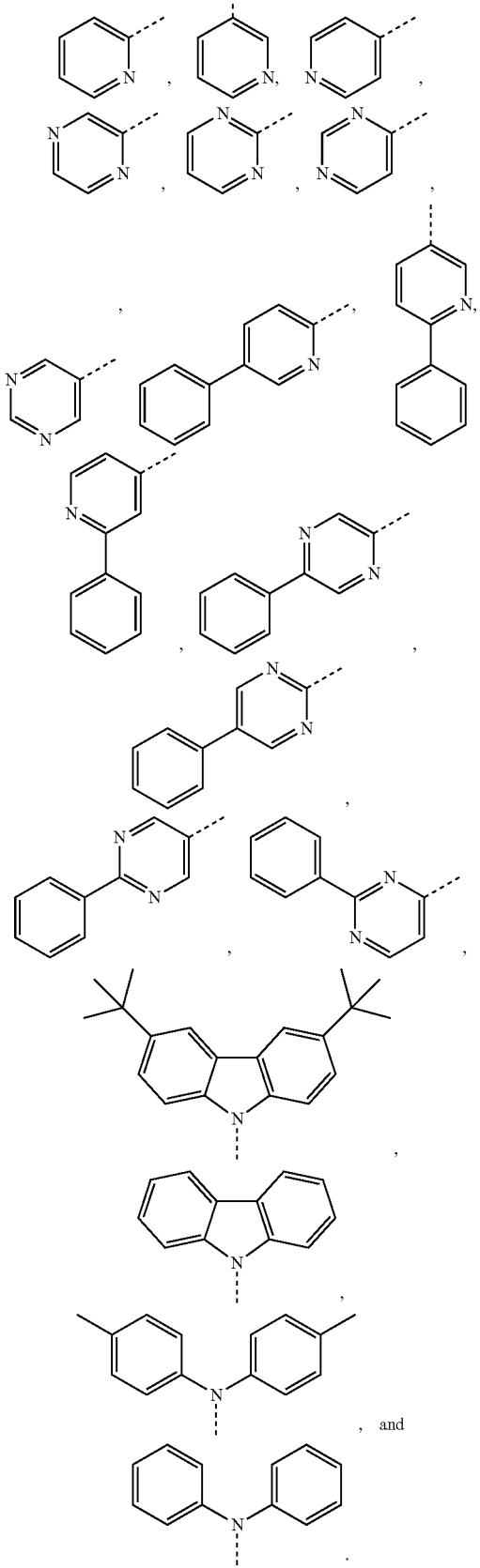

, and

In one embodiment, the cyclic group comprises a heteroatom, and the heteroatom is selected from O, S, or N.

In one embodiment, the cyclic group is selected from one of formulas as follows:

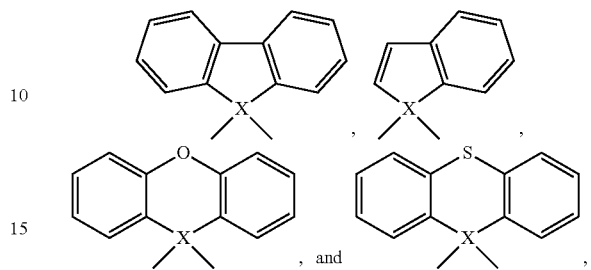

, and and X is selected from C or Si.

A method of synthesizing the fluorescent material comprises steps as follows:

making a reactant of formula (2) undergo a cyclization reaction with a catalyst to obtain the fluorescent material, and the formula (2) is present as follows:

formula (2)

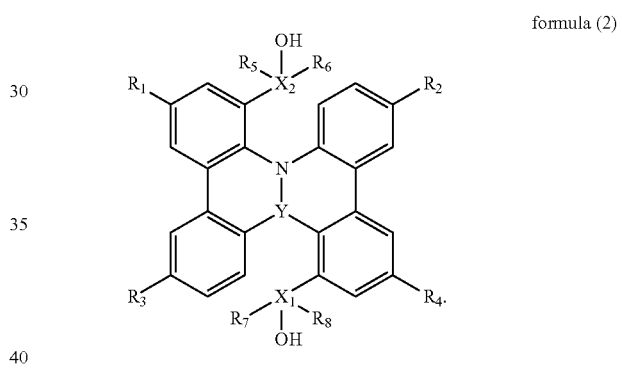

In one embodiment, $R_1$, $R_2$, $R_3$, $R_4$, $R_5$, $R_6$, $R_7$, and $R_5$ are selected from $C_6$-$C_{50}$ an aromatic hydrocarbon group, a heteroaryl group, a $C_1$-$C_{20}$ alkyl group; or $R_5$ and $R_6$ form a $C_6$-$C_{50}$ cyclic group; or $R_7$ and $R_8$ form a $C_6$-$C_{50}$ cyclic group.

In one embodiment, $R_5$ and $R_6$ form a $C_6$-$C_{50}$ cyclic group having an aryl substituent; or $R_7$ and $R_8$ form a $C_6$-$C_{50}$ cyclic group having an aryl substituent.

In one embodiment, $R_1$, $R_2$, $R_3$, $R_4$, $R_5$, $R_6$, $R_7$, and $R_8$ are selected from one of formulas as follows:

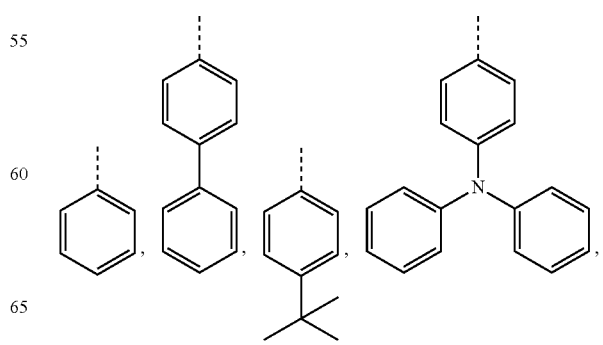

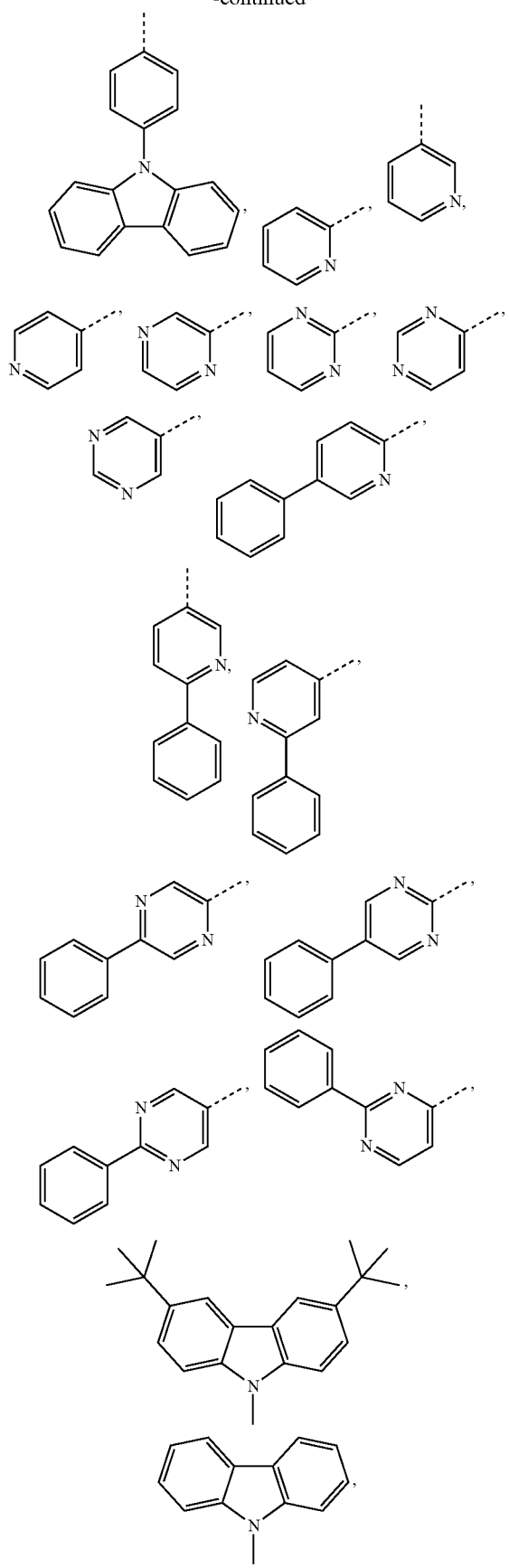

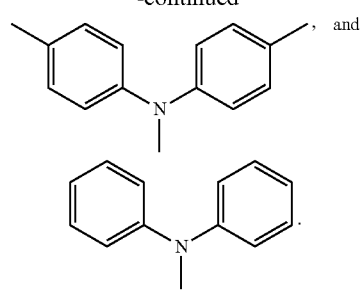

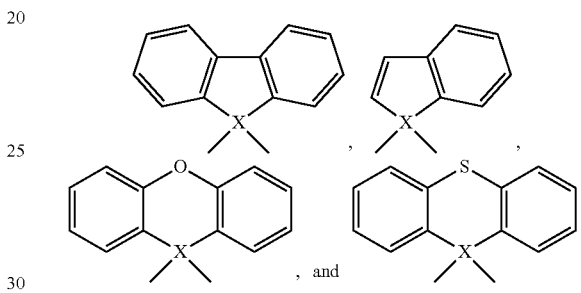

In one embodiment, the cyclic group comprises a heteroatom, and the heteroatom is selected from O, S, or N.

In one embodiment, the cyclic group is selected from one of formulas as follows:

and X is selected from C or Si.

In one embodiment, the catalyst is an acid catalyst.

In one embodiment, the catalyst comprises concentrated hydrochloric acid and glacial acetic acid, and heating or reflux assisting is performed for 12-48 hours during the cyclization reaction.

An electroluminescent device comprises a first electrode, a light-emitting layer, and a second electrode, and the light-emitting layer comprises the fluorescent material.

The present invention has beneficial effects described herein. Two acridines are connected in a plane to form a class of organic fluorescent materials with a rigid planar structure. The rigid planar structure can reduce molecular vibration, so the interaction between molecules and solvents or other solute molecules is reduced. Also, it reduces the possibility of collision deactivation, makes the fluorescent material have strong fluorescent properties, and improves the quantum efficiency of the material.

In the embodiments of the present invention, the fluorescent material can be applied to the light-emitting layer of an organic electroluminescent device. The maximum external quantum efficiency of the organic electroluminescent device can reach 16%, and the device efficiency is also improved.

In the embodiments of the present invention, the method of synthesizing the fluorescent material is simple, avoids the use of rare metals, and has huge application prospects in the field of OLEDs.

DETAILED DESCRIPTION OF SPECIFIC EMBODIMENTS OF THE INVENTION

Figure 1:
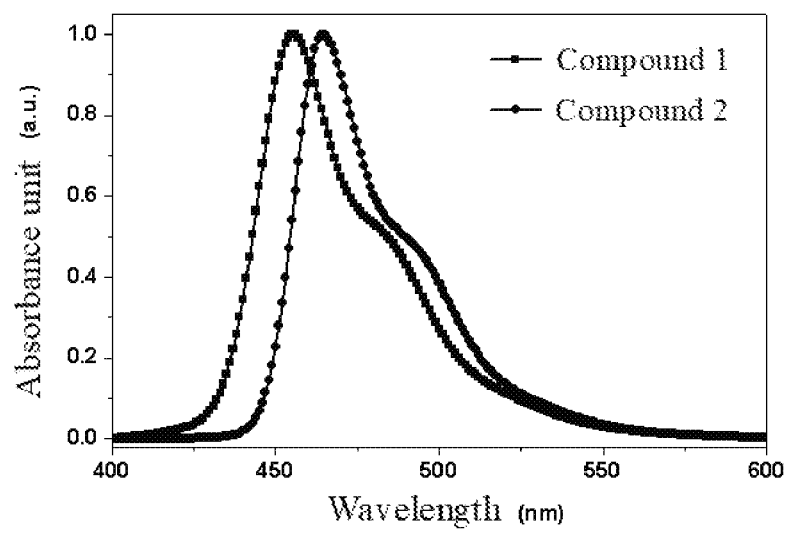
FIG. 1 is a fluorescence spectrum of target fluorescent compounds provided in first embodiment and second embodiment of the present invention.

First, the definition and clarification of terms are proposed, followed by the deep-blue fluorescent material represented by formula (1), and the embodiments.

Definition and clarification of terms are described as follows.

Before presenting the details of the following embodiments, some terms are defined or clarified.

The term "alkyl group" refers to a group derived from an aliphatic hydrocarbon and includes linear, branched, or cyclic groups. In some embodiments, the alkyl group has from 1 to 20 carbon atoms.

The term "aryl group" refers to a moiety derived from an aromatic compound. The expression "derived from a compound" means a group formed by removing one or more hydrogen or deuterium. The aryl group may be a single ring or have multiple rings fused together or covalently linked.

The term "hydrocarbon aryl group" refers to having only carbon atoms in one or more aromatic rings.

The term "heteroaryl group" refers to having one or more heteroatoms in an aromatic ring.

In some embodiments, the aryl group, the hydrocarbon aryl group, or the heteroaryl group has 6 to 50 carbon atoms; in some embodiments, the aryl group, hydrocarbon aryl group, or heteroaryl group has 6 to 30 carbon atoms.

All groups may be substituted or unsubstituted.

Unless otherwise defined, all technical and scientific terms used herein have the same meaning as commonly understood by those of ordinary skill in the art to which this application belongs. Although methods and materials similar or equivalent to those described herein can be used in the practice or testing of embodiments of the present application, suitable methods and materials are described below. In addition, the materials, methods, and embodiments are merely exemplary and are not intended to be limiting.

A fluorescent material includes a formula (1) as follows:

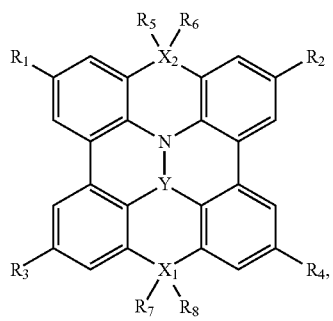

formula (1)

and Y is N or B; $X_1$ and $X_2$ are the same or different; $X_1$ and $X_2$ are selected from C or Si; $R_1$, $R_2$, $R_3$, and $R_4$ are the same or different; $R_1$, $R_2$, $R_3$, and $R_4$ are selected from a hydrogen atom, an alkyl group, an aromatic hydrocarbon group, or a heteroaryl group; $R_5$, $R_6$, $R_7$, and $R_8$ are the same or different; $R_5$, $R_6$, $R_7$, and $R_8$ are selected from an alkyl group, an aromatic hydrocarbon group, or a heteroaryl group; or $R_5$ and $R_6$ form a cyclic group; or $R_7$ and $R_8$ form a cyclic group.

In one embodiment, $R_1$, $R_2$, $R_3$, $R_4$, $R_5$, $R_6$, $R_7$, and $R_8$ are selected from $C_6$-$C_{50}$ an aromatic hydrocarbon group, a heteroaryl group, a $C_1$-$C_{20}$ alkyl group; or $R_5$ and $R_6$ form a $C_6$-$C_{50}$ cyclic group; or $R_7$ and $R_8$ form a $C_6$-$C_{50}$ cyclic group.

In one embodiment, $R_5$ and $R_6$ form a $C_6$-$C_{50}$ cyclic group having an aryl substituent; or $R_7$ and $R_8$ form a $C_6$-$C_{50}$ cyclic group having an aryl substituent.

In one embodiment, $R_1$, $R_2$, $R_3$, $R_4$, $R_5$, $R_6$, $R_7$, and $R_8$ are selected from one of formulas as follows:

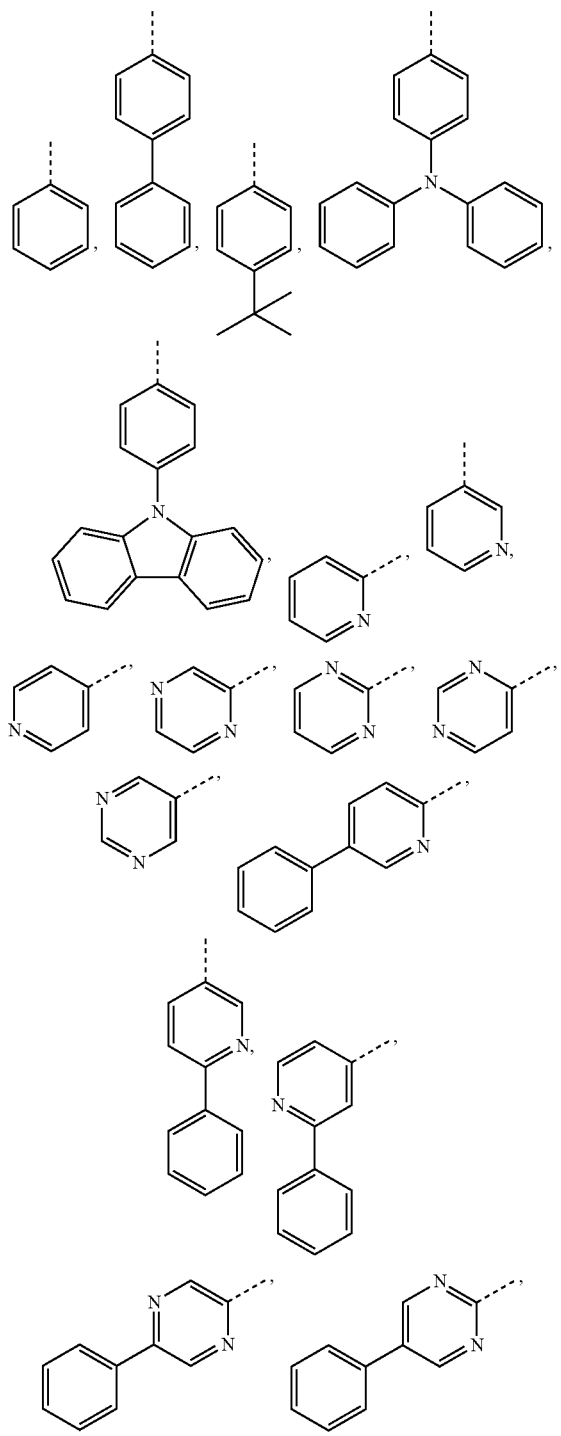

-continued

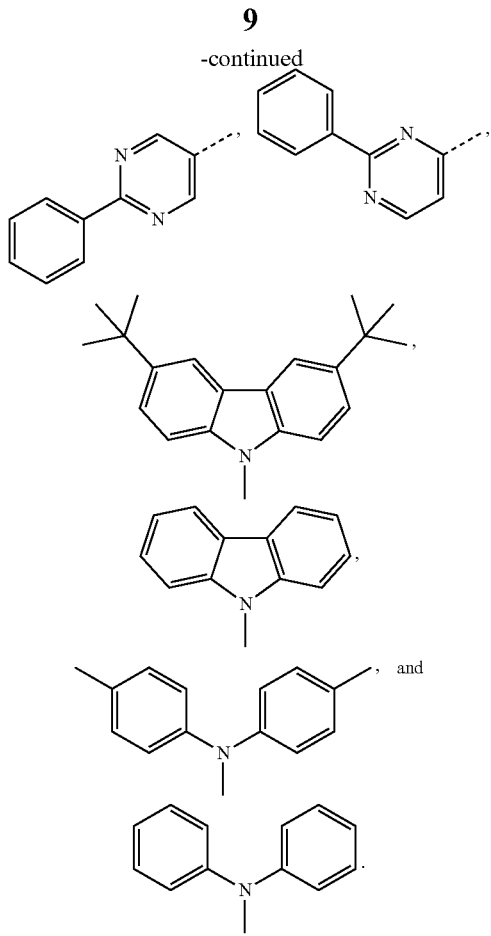

In one embodiment, the cyclic group comprises a heteroatom, and the heteroatom is selected from O, S, or N.

In one embodiment, the cyclic group is selected from one of formulas as follows:

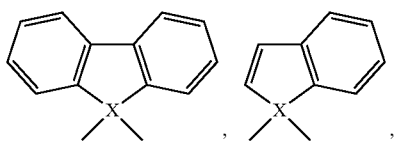

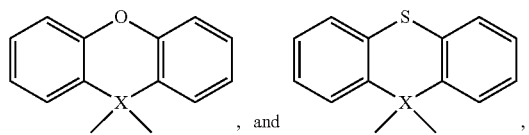

and X is selected from C or Si.

In one embodiment, a method of synthesizing the fluorescent material of claim 1 includes steps as follows:

making a reactant of formula (2) undergo a cyclization reaction with a catalyst, and then cooling, extracting, drying, and filtering, concentrating, separating, and purifying to obtain the fluorescent material, and reactant of the formula (2) is presented as follows:

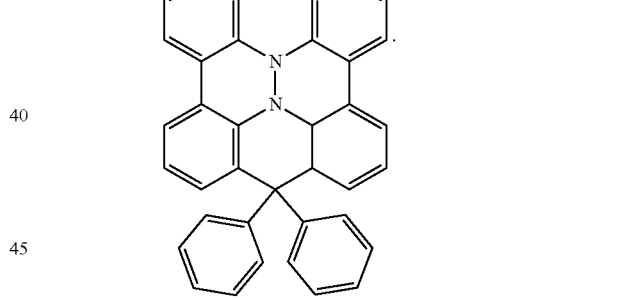

formula (2)

In one embodiment, the catalyst includes concentrated hydrochloric acid and glacial acetic acid. A volume ratio of the concentrated hydrochloric acid to the glacial acetic acid is 100:1 to 1:100, and a volume ratio of the amount of reactant to the concentrated hydrochloric acid is 0.01-100 mol/L.

In one embodiment, heating or reflux assisting is performed for 12-48 hours during the cyclization reaction.

In first embodiment, a deep-blue fluorescent material (target compound 1) is presented by formula (1-a)

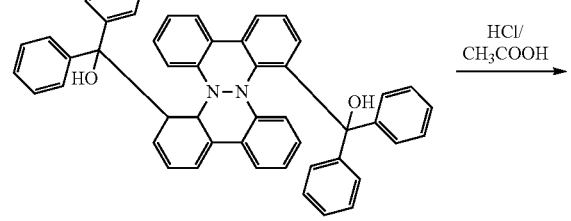

The synthetic route of the target compound 1 is shown as follows:

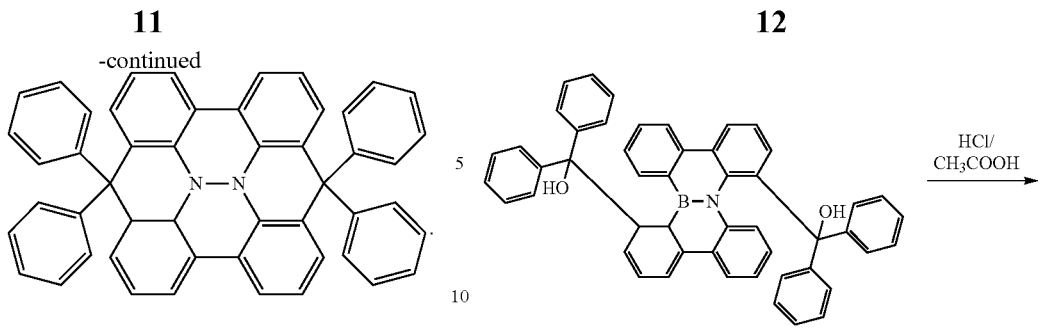

The synthesis method includes the following steps: the reactant (6.99 g, 10 mmol) presented by formula (2-a)

5 mL concentrated hydrochloric acid, and 15 mL glacial acetic acid are added into a 50 mL reaction vessel, and then the reaction is performed at 120° C. for 24 h. After cooling, pour into ice water, add 1 mol/L sodium bicarbonate solution to neutralize the acid, and then extract three times with dichloromethane (DCM), wash three times with water, dry over anhydrous sodium sulfate, filter, and concentrate. Column chromatograph is carried out by using silica gel (200-300 mesh), and petroleum ether/DCM (4:1, V/V) is used as an eluent, so 5.43 g white solid target compound 1 is obtained in 82% yield. Product identification data: 1HRMS [M+H]+ calcd. for $C_{50}H_{34}N_2$: 662.2722; found: 662.2734.

In second embodiment, a deep-blue fluorescent material (target compound 2) is presented by formula (1-b)

The synthetic route of the target compound 2 is shown as follows:

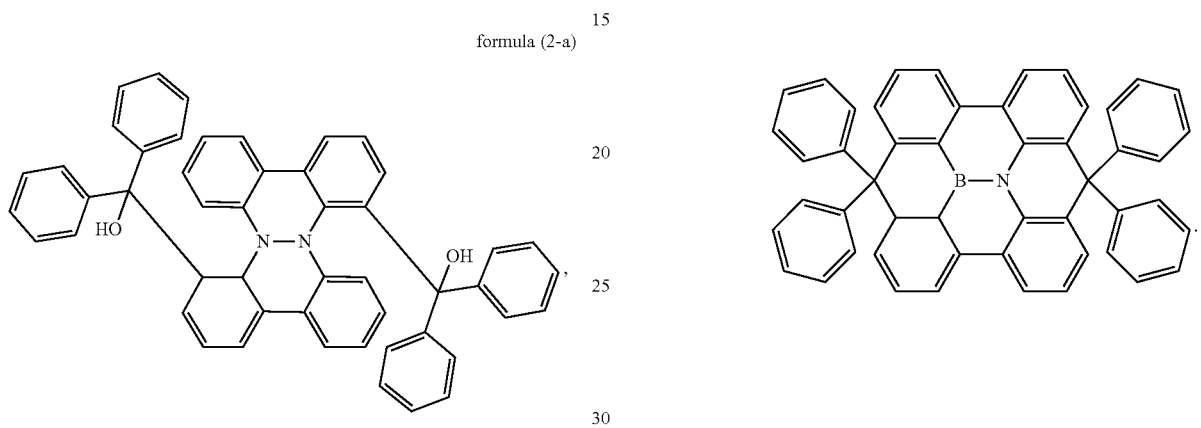

The synthesis method includes the following steps: the reactant (6.99 g, 10 mmol) presented by formula (2-b)

5 mL concentrated hydrochloric acid, and 15 mL glacial acetic acid are added into a 50 mL reaction vessel, and then the reaction is performed at 120° C. for 24 h. After cooling, pour into ice water, add 1 mol/L sodium bicarbonate solution to neutralize the acid, and then extract three times with dichloromethane (DCM), wash three times with water, dry over anhydrous sodium sulfate, filter, and concentrate. Column chromatograph is carried out by using silica gel (200-300 mesh), and petroleum ether/DCM (4:1, V/V) is used as an eluent, so 5.43 g white solid target compound 2 is obtained in 82% yield. Product identification data: 1HRMS [M+H]+ calcd. for $C_{50}H_{34}BN$: 659.2784; found: 659.2798.

In third embodiment, photophysical test and analysis are performed on the target compound 1, compound 2, and the traditional fluorescent material (Ref) presented by

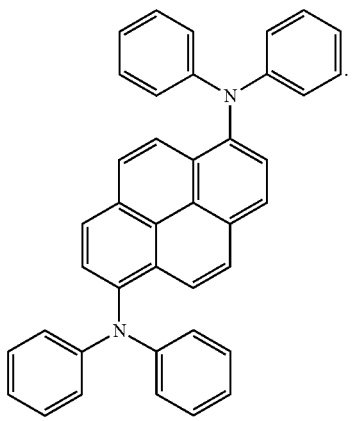

formula (3)

The fluorescence emission spectrum is shown in FIG. 1. The other parameters such as electrochemical energy levels of the target compound 1, target compound 2, and Ref are measured. The lowest singlet state (S1) and lowest triplet energy level (T1), energy level difference, and photoluminescence quantum efficiency (PLQY) of target compound 1, target compound 2, and Ref are shown in Table 1.

S1 is measured by room temperature fluorescence spectroscopy, T1 is measured by low temperature (77K) phosphorescence spectroscopy, and highest occupied molecular orbital (HOMO) and lowest unoccupied molecular orbital (LUMO) are measured by electrochemical redox. Photoluminescence spectrum refers to PL spectrum. PL peak refers to the strongest emission peak of the photoluminescence spectrum. PLQY is measured by means of Absolute PL Quantum Yield Measurement C9920-03G system of Hamamatsu Photonics. PLQY refers to photoluminescence quantum yield, which represents the ability of a substance to emit fluorescence and is usually expressed by the following formula: PLQY %=number of fluorescence emitting molecules/total number of excited molecules.

Table 1 shows the lowest singlet state (S1), lowest triplet energy level (T1), energy level difference, and PLQY of target compound, 1, target compound 2, and Ref.

TABLE 1

|  | PL Peak (nm) | $S_1$ (eV) | $T_1$ (eV) | $\Delta(2T_1 - S_1)$ (eV) | PLQY (%) |
|---|---|---|---|---|---|
| Target compound 1 | 455 | 2.72 | 1.64 | 0.54 | 94 |
| Target compound 2 | 464 | 2.67 | 1.61 | 0.55 | 96 |
| Ref | 465 | 2.66 | 1.64 | 0.62 | 90 |

It can be seen from FIG. 1 and Table 1 that the emission wavelength of the target compound 1 is 455 nm, and the emission wavelength of the target compound 2 is 464 nm, both of which emit good deep blue light. Since nitrogen (N) is an electron-donating atom and boron is an electron-withdrawing atom, the boron-nitrogen bond will cause a certain degree of HOMO and LUMO separation in the entire molecule. Due to the symmetrical structure of the N—N bond molecules, the spectrum is not influenced greatly, and the introduction of boron atoms will cause a minor red-shift in the spectrum.

Target compound 1 and target compound 2 have obvious triplet-triplet annihilation effect. When T1 value is twice greater than S1, it ensures that triplet-triplet annihilation can occur. When two triplet molecules reach a certain concentration, the triplet-triplet annihilation between the two molecules will occur. One molecule transitions back to the ground state, and the other molecule is excited to a singlet excited state with a higher energy level. Molecules in the singlet excited state retreat to the ground state in the form of a radiation transition and emit blue-light at the same time.

Compared with the traditional fluorescent material (Ref), the target compound 1 and the target compound 2 have higher luminescence quantum efficiency, which are 94% and 96%. Due to their larger rigid planar structure, it may effectively suppress non-radiative transitions, and the radiation rate constant is increased, thereby providing an improved photoluminescence quantum yield of the material. At the same time, nitrogen atoms and boron atoms can increase the probability of intersystem transition from singlet excited state to triplet excited state.

The molecule of the fluorescent material includes a nitrogen atom. Because the nitrogen atom has an empty p orbital, it can form a p-π conjugation with the benzene ring, which enhances the degree of conjugation of the π electron, increases the probability of transition between the lowest excited singlet state and the ground state, and promotes the fluorescent material to emit light efficiently. The boron atom in the target compound 2 makes a highly electron-deficient structure have strong electron-withdrawing properties. The nitrogen-boron bond has high bond energy, and its structure is stable, and thus it can form a type of fluorescent material with triple-triple annihilation (TTA), high quantum efficiency, and good luminous color.

Figure 2:
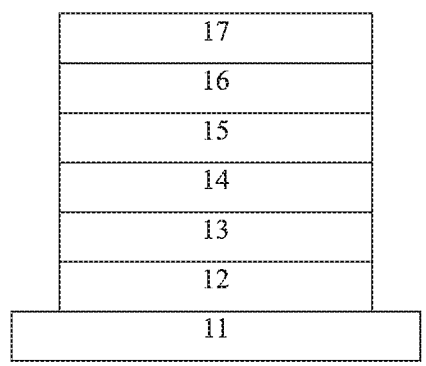
FIG. 2 is a schematic structural view of a manufactured electroluminescent device in third embodiment of the present invention.

In fourth embodiment, an organic electroluminescent device is provided. As shown in FIG. 2, which includes a first electrode 11, a hole injection layer 12, a hole transport layer 13, a light-emitting layer 14, an electron transport layer 15, an electron injection layer 16, and a second electrode 17 disposed in order from bottom to top. The first electrode 11 is a conductive glass (ITO) substrate. The hole injection layer 12 is HATCN. The hole transport layer 13 is NPB. The light-emitting layer 14 includes the target compound 1, the target compound 2, or a traditional fluorescent material (Ref) as a guest material. The gust material is luminescent material. The electron transport layer 15 is TPBI. The electron injection layer 16 is LiF. The second electrode 17 is Al. The manufacturing method refers to Chem. Sci., 2016, 7, 4044-4051, and target device 1, target device 2, and comparative device are obtained.

Target device 1: ITO (150 nm)/HATCN (10 nm)/NPB (20 nm)/host: (2%) target compound 1 (30 nm)/TPBI (10 nm)/LiF (1 nm)/Al (100 nm).

Target device 2: ITO (150 nm)/HATCN (10 nm)/NPB (20 nm)/host: (2%) target compound 2 (30 nm)/TPBI (10 nm)/LiF (1 nm)/Al (100 nm).

Comparative device: ITO (150 nm)/HATCN (10 nm)/NPB (20 nm)/host: (2%) Ref (30 nm)/TPBI (10 nm)/LiF (1 nm)/Al (100 nm).

Test the performance of target device 1, the target device 2, and the comparative device. The current-brightness-voltage characteristics of the devices are measured by a Keithley source measurement system (Keithley 2400 Sourcemeter, Keithley 2000 Currentmeter) with a corrected silicon photodiode, and the electroluminescence spectrum is measured by SPEX CCD3000 spectrometer of French JY Company. All measurements are done in room temperature and normal atmosphere.

The test results are shown in Table 2. Electroluminescence (EL: Electroluminescence) emission spectrum and EL peak represent the strongest emission peak of electroluminescence emission spectrum.

A full width at half maximum of the emission spectra, a wavelength of the strongest emission peak, and a maximum external quantum efficiency of the target device 1, the target device 2, and the comparative device are shown in Table 2.

| Device | FWHM (nm) | EL peak (nm) | A maximum external quantum efficiency (%) | Service life (hrs) @1000 cd/m² |
|---|---|---|---|---|
| Target device 1 | 37 | 458 | 15 | 250 |
| Target device 2 | 32 | 461 | 16 | 310 |
| Comparative device | 39 | 465 | 12 | 200 |

It can be seen from Table 2 that the target device 1 and the target device 2 manufactured by using the target compound 1 and the target compound 2 as the light-emitting layer have good device performance compared with the comparative device. The wavelengths of the strongest emission peaks are 458 nm and 461 nm, and the full widths at half maximum are 37 nm and 32 nm. It shows that the emission color of the target device 1 and the target device 2 is blue light. The blue emission peak is narrow and the color purity is good. The maximum external quantum efficiency of the two target devices is as high as 15% and 16%. The service lives of the target device 1, the target device 2, and the comparative device are measured at 1000 cd/m². The fluorescent material used as a guest material is doped in the host material as a light-emitting layer, which improves the luminescence life of the device. The above-mentioned data completely shows that fluorescent material containing a planar structure made of nitrogen-nitrogen or nitrogen-boron bonds is feasible and may be served as light-emitting materials. The fluorescent material has good energy transfer with the host material, and is also a deep-blue guest material with excellent performance.

In the above, the present application has been described in the above preferred embodiments, but the preferred embodiments are not intended to limit the scope of the invention, and a person skilled in the art may make various modifications without departing from the spirit and scope of the application. The scope of the present application is determined by claims.

What is claimed is:

1. A fluorescent material, comprising a formula (1) as follows:

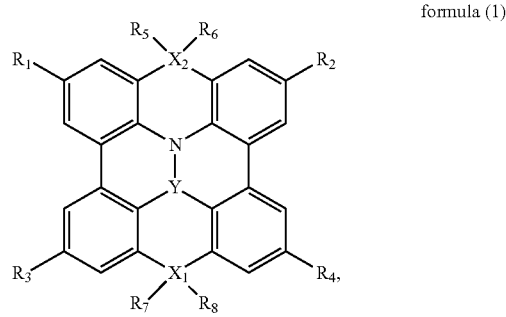

formula (1)

wherein Y is N or B; $X_1$ and $X_2$ are the same or different; $X_1$ and $X_2$ are selected from C or Si; $R_1$, $R_2$, $R_3$, $R_4$, $R_5$, $R_6$, $R_7$, and $R_8$ are the same or different; $R_1$, $R_2$, $R_3$, $R_4$, $R_5$, $R_6$, $R_7$, and $R_8$ are selected from a $C_6$-$C_{50}$ aromatic hydrocarbon group, a heteroaryl group, a $C_1$-$C_{20}$ alkyl group; or $R_5$ and $R_6$ form a $C_6$-$C_{50}$ cyclic group; or $R_7$ and $R_8$ form a $C_6$-$C_{50}$ cyclic group, wherein at least one of the following is true;

i) $R_5$ and $R_6$ form a $C_6$-$C_{50}$ cyclic group having an aryl substituent; or $R_7$ and $R_8$ form a $C_6$-$C_{50}$ cyclic group having an aryl substituent ii) $R_5$ and $R_6$ form a $C_6$-$C_{50}$ cyclic group or $R_7$ and $R_8$ form a $C_6$-$C_{50}$ cyclic group and the cyclic group is selected from one of the formulas as follows:

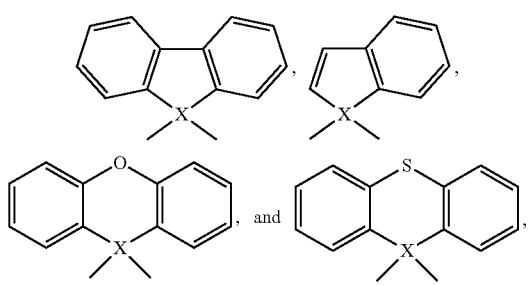

and X represents the $X_1$ or $X_2$ and is selected from C or Si.

2. The fluorescent material according to claim 1, wherein $R_1$, $R_2$, $R_3$, and $R_4$ are selected from one of formulas as follows:

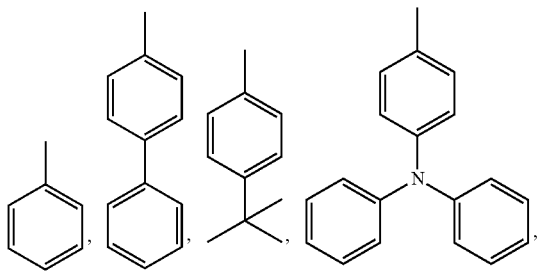

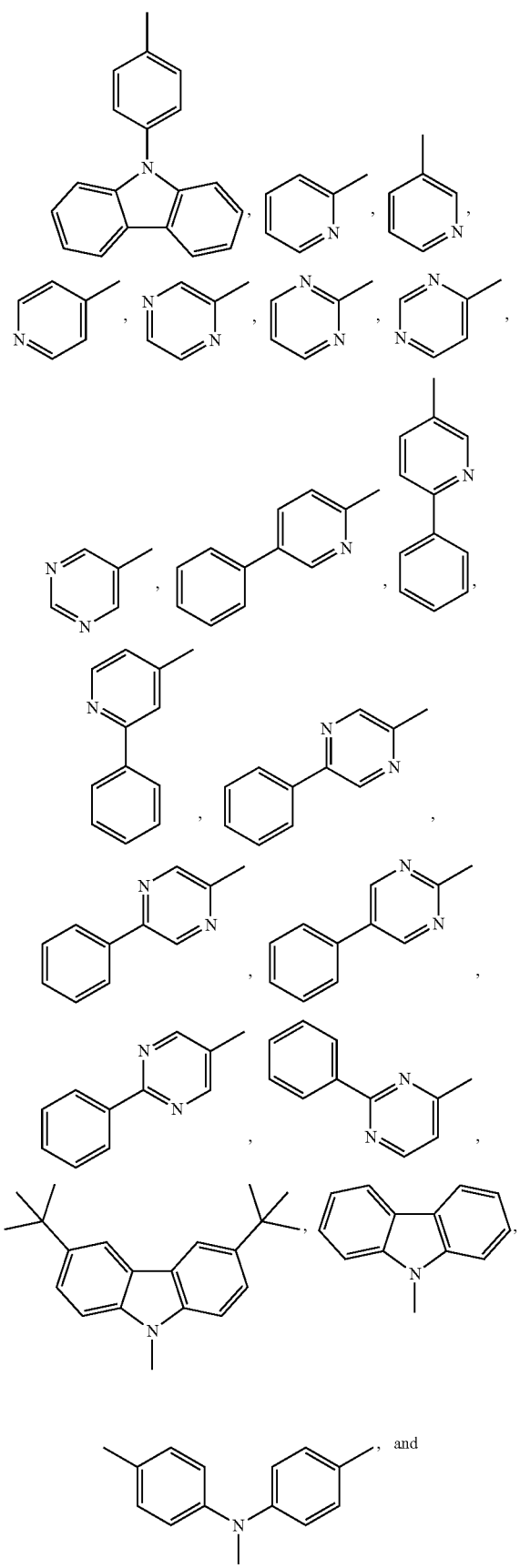

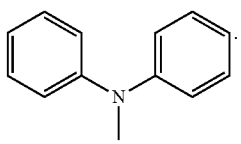

3. The fluorescent material according to claim 1, wherein the cyclic group comprises a heteroatom, and the heteroatom is selected from O, S, or N.

4. A method of synthesizing the fluorescent material of claim 1, comprising steps as follows:
   making a reactant of formula (2) undergo a cyclization reaction with a catalyst to obtain the fluorescent material, wherein the reactant of formula (2) is presented as follows:

formula (2)

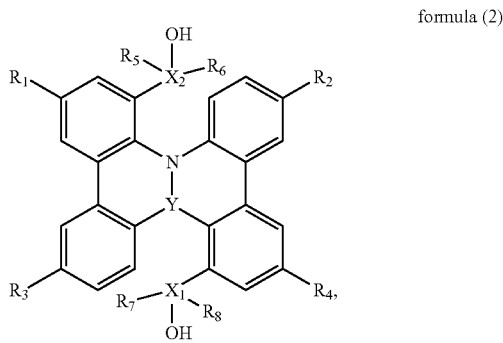

wherein $R_1$, $R_2$, $R_3$, $R_4$, $R_5$, $R_6$, $R_7$, and $R_8$ are selected from a $C_6$-$C_{50}$ aromatic hydrocarbon group, a heteroaryl group, a $C_1$-$C_{20}$ alkyl group; or $R_5$ and $R_6$ form a $C_6$-$C_{50}$ cyclic group; or $R_7$ and Re form a $C_6$-$C_{50}$ cyclic group, wherein at least one of the following is true:
   i) $R_5$ and $R_6$ form a $C_6$-$C_{50}$ cyclic group having an aryl substituent; or $R_7$ and $R_8$ form a $C_6$-$C_{50}$ cyclic group having an aryl substituent
   ii) $R_5$ and $R_6$ form a $C_6$-$C_{50}$ cyclic group or $R_7$ and $R_8$ form a $C_6$-$C_{50}$ cyclic group and the cyclic group is selected from one of the formulas as follows:

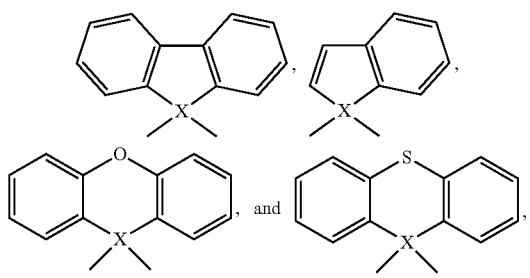

and X represents the $X_1$ or $X_2$ and is selected from C or Si.

5. The method of synthesizing the fluorescent material according to claim 4, wherein $R_1$, $R_2$, $R_3$, and $R_4$ are selected from one of formulas as follows:

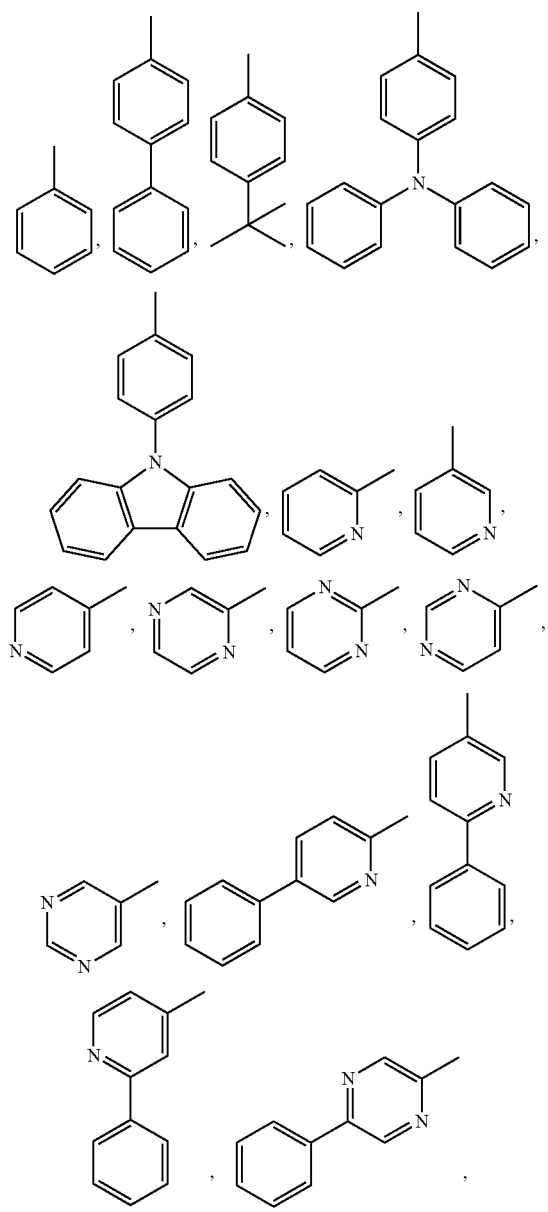

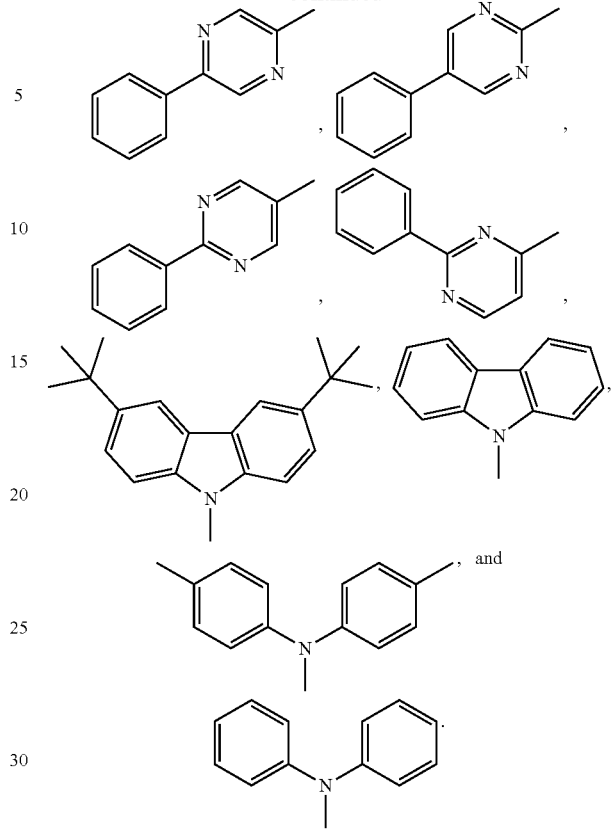

6. The method of synthesizing the fluorescent material according to claim 4, wherein the cyclic group comprises a heteroatom, and the heteroatom is selected from O, S, or N.

7. The method of synthesizing the fluorescent material according to claim 4, wherein the catalyst is an acid catalyst.

8. The method of synthesizing the fluorescent material according to claim 4, wherein the catalyst comprises concentrated hydrochloric acid and glacial acetic acid, and heating or reflux assisting is performed for 12-48 hours during the cyclization reaction.

9. An electroluminescent device, comprising a first electrode, a light-emitting layer, and a second electrode, wherein the light-emitting layer comprises the fluorescent material of claim 1.

\* \* \* \* \*